United States Patent
Johnson et al.

(10) Patent No.: US 12,357,807 B2
(45) Date of Patent: Jul. 15, 2025

(54) MEDICAL TUBE SECUREMENT DEVICE

(71) Applicants: Alexander Johnson, Heber City, UT (US); Phillip Whiting, Vienna, VA (US)

(72) Inventors: Alexander Johnson, Heber City, UT (US); Phillip Whiting, Vienna, VA (US)

( * ) Notice: Subject to any disclaimer, the term of this patent is extended or adjusted under 35 U.S.C. 154(b) by 947 days.

(21) Appl. No.: 17/381,189

(22) Filed: Jul. 20, 2021

(65) Prior Publication Data
US 2022/0023608 A1    Jan. 27, 2022

Related U.S. Application Data

(60) Provisional application No. 63/054,741, filed on Jul. 21, 2020.

(51) Int. Cl.
*A61M 39/10* (2006.01)
*A61M 16/04* (2006.01)

(52) U.S. Cl.
CPC .... *A61M 39/1011* (2013.01); *A61M 16/0493* (2014.02); *A61M 16/0497* (2013.01); *A61M 2039/1077* (2013.01)

(58) Field of Classification Search
CPC .... A61M 2025/024; A61M 39/28–288; A61M 5/1418; A61M 39/1011; A61M 16/0493; A61M 16/0497; A61M 2039/1077; F16L 3/01; A61J 15/0053; A61J 15/0061; A61J 15/0065

See application file for complete search history.

(56) References Cited

U.S. PATENT DOCUMENTS

| | | | | |
|---|---|---|---|---|
| 2,586,940 A * | 2/1952 | Graham | ........... | A61M 25/02 604/179 |
| 3,924,636 A * | 12/1975 | Addison | ........... | A61M 16/0488 128/207.14 |
| 3,946,742 A * | 3/1976 | Eross | ........... | A61M 25/02 128/DIG. 26 |
| 4,270,529 A | 6/1981 | Muto | | |
| 4,284,076 A * | 8/1981 | Hall | ........... | A61M 25/02 128/207.18 |

(Continued)

FOREIGN PATENT DOCUMENTS

| | | | | |
|---|---|---|---|---|
| CN | 109937066 A | * | 6/2019 | ........... A61M 16/04 |
| CN | 110585028 A | * | 12/2019 | |

OTHER PUBLICATIONS

English translation for CN 109937066, machine translated by Espacenet.com, translated on Nov. 26, 2024.*

(Continued)

*Primary Examiner* — Tu A Vo
(74) *Attorney, Agent, or Firm* — Kunzler Bean & Adamson (57) ABSTRACT

An apparatus for a medical tube securement device includes a base member and a clamp member. The base member includes a first tab portion, a second tab portion, and an opening for receiving a tube. The opening is located substantially between the first tab portion and the second tab portion. A clamp member secures the tube within the opening to prevent the tube from moving while the base member is attached to a person and the tube is located at a tube insertion site on the person.

16 Claims, 7 Drawing Sheets

(56) References Cited

U.S. PATENT DOCUMENTS

| | | | | |
|---|---|---|---|---|
| 4,516,293 | A | * | 5/1985 | Beran .................. A61M 25/02 |
| | | | | 24/17 AP |
| 4,699,616 | A | * | 10/1987 | Nowak ................ A61M 25/02 |
| | | | | 128/DIG. 26 |
| 4,774,944 | A | | 10/1988 | Mischinski |
| 4,986,815 | A | * | 1/1991 | Schneider ............ A61M 25/02 |
| | | | | 604/178 |
| 5,009,227 | A | * | 4/1991 | Nieuwstad ........ A61M 16/0497 |
| | | | | 128/207.14 |
| 5,069,206 | A | | 12/1991 | Crosbie |
| 5,237,988 | A | * | 8/1993 | McNeese .......... A61M 16/0497 |
| | | | | 24/306 |
| 5,305,742 | A | | 4/1994 | Styers et al. |
| 5,490,504 | A | * | 2/1996 | Vrona ............... A61M 16/0488 |
| | | | | 128/207.14 |
| 5,551,421 | A | * | 9/1996 | Noureldin ......... A61M 16/0488 |
| | | | | 604/179 |
| 5,653,232 | A | * | 8/1997 | Rogers .............. A61M 16/0488 |
| | | | | 128/207.14 |
| 5,803,079 | A | * | 9/1998 | Rogers ................ A61M 25/02 |
| | | | | 128/207.14 |
| 6,578,576 | B1 | * | 6/2003 | Taormina ............. A61M 25/02 |
| | | | | 128/207.14 |
| 6,755,191 | B2 | | 6/2004 | Bertoch et al. |
| 7,063,088 | B1 | * | 6/2006 | Christopher ...... A61M 16/0493 |
| | | | | 128/207.14 |
| 7,802,574 | B2 | | 12/2010 | Schultz |
| 8,074,650 | B2 | | 12/2011 | Steeves et al. |
| 8,863,746 | B2 | | 10/2014 | Totz |
| 9,233,228 | B1 | | 1/2016 | Lelievre et al. |
| 10,398,629 | B1 | | 9/2019 | Spironello |
| 10,398,866 | B1 | | 9/2019 | Ekstam |
| 10,500,361 | B2 | | 12/2019 | Phillips et al. |
| 2001/0029954 | A1 | * | 10/2001 | Palmer ............... A61M 16/0688 |
| | | | | 128/207.18 |
| 2002/0092526 | A1 | * | 7/2002 | Bertoch ............ A61M 16/0497 |
| | | | | 128/206.29 |
| 2002/0189614 | A1 | * | 12/2002 | Dominguez ...... A61M 16/0488 |
| | | | | 128/200.26 |
| 2003/0034036 | A1 | | 2/2003 | Waldeck |
| 2005/0038453 | A1 | * | 2/2005 | Raulerson ............. A61M 25/02 |
| | | | | 606/151 |
| 2005/0133038 | A1 | * | 6/2005 | Rutter ............... A61M 16/0497 |
| | | | | 128/207.17 |
| 2006/0118120 | A1 | * | 6/2006 | Russo ............... A61M 16/0497 |
| | | | | 128/207.14 |
| 2007/0068533 | A1 | | 3/2007 | Bierman et al. |
| 2008/0092349 | A1 | * | 4/2008 | Cofer .................. A61M 5/1418 |
| | | | | 24/487 |
| 2011/0108038 | A1 | | 5/2011 | Pierson |
| 2011/0240034 | A1 | * | 10/2011 | Ciccone ........... A61M 16/0493 |
| | | | | 128/207.17 |
| 2013/0233322 | A1 | | 9/2013 | Jatana et al. |
| 2014/0261463 | A1 | * | 9/2014 | Visconti ............ A61B 1/00154 |
| | | | | 128/861 |
| 2016/0095995 | A1 | * | 4/2016 | Haider ............. A61M 16/0493 |
| | | | | 128/207.14 |
| 2016/0121067 | A1 | | 5/2016 | VanMiddendorp et al. |
| 2017/0182276 | A1 | * | 6/2017 | Hammer .......... A61M 16/0683 |
| 2018/0021507 | A1 | * | 1/2018 | Tamrazi ................ A61M 25/09 |
| | | | | 24/16 R |
| 2018/0344960 | A1 | | 12/2018 | Kaneyasu |
| 2019/0070378 | A1 | * | 3/2019 | Kanowitz ......... A61M 16/0463 |
| 2019/0353281 | A1 | * | 11/2019 | Wakabayashi ........ A61M 16/08 |
| 2019/0381267 | A1 | | 12/2019 | De Oliveira et al. |
| 2019/0388303 | A1 | * | 12/2019 | Sharaiha ............. A61J 15/0003 |
| 2020/0009342 | A1 | * | 1/2020 | Drew .................... A61B 90/57 |
| 2021/0093818 | A1 | * | 4/2021 | Shantha ........... A61M 16/0495 |
| 2021/0187229 | A1 | * | 6/2021 | Brar ................. A61M 16/0493 |

OTHER PUBLICATIONS

English translation for CN 110585028, machine translated by Espacenet.com, translated on Nov. 26, 2024.*

* cited by examiner

MEDICAL TUBE SECUREMENT DEVICE

CROSS-REFERENCES TO RELATED APPLICATIONS

This application claims the benefit of U.S. Provisional Patent Application No. 63/054,741 entitled "MEDICAL TUBE SECUREMENT DEVICE" and filed on Jul. 21, 2020, for Alexander Johnson and Phillip Whiting, which is incorporated herein by reference.

FIELD

This invention relates to medical devices and more particularly relates to medical tube securement devices.

BACKGROUND

Medical tubes have various applications in medicine, including insertion into a person's body in many different ways for many different reasons; however, securing a tube at a location on a person's body can be cumbersome.

SUMMARY

Apparatuses, systems, and methods are disclosed for a medical tube securement device.

An apparatus for a medical tube securement device, in one embodiment, includes a base member and a clamp member. In one embodiment, the base member includes a first tab portion, a second tab portion, and an opening for receiving a tube. In certain embodiments, the opening is located substantially between the first tab portion and the second tab portion.

A clamp member, in one embodiment, secures the tube within the opening to prevent the tube from moving while the base member is attached to a person and the tube is located at a tube insertion site on the person.

In some embodiments, the clamp member comprises a first arm and a second arm opposite the first arm. The first and second arms may each comprise at least one prong that, when the first and second arms apply clamping force to the tube, interlace around the tube to secure the tube within the opening in the base member.

In one embodiment, the clamp arms are configured to secure tubes having various sizes within the opening in the base member. In various embodiments, the clamp arms are configured to secure generic medical tubes that have internal diameters within a range of 5 millimeters to 8 millimeters.

In further embodiments, the clamp member is fastened to the base member using a fastening member such that first and second arms are rotatable about the fastening member. In some embodiments, the clamp member includes a torsion spring that is coupled to both a first and second arms and that is configured to cause the first and second arms to maintain pressure against the tube when the tube is clamped between the first and second arms.

In one embodiment, the opening of the base member comprises a u-shaped groove. In various embodiments, the base member is made of a hypoallergenic plastic material. In further embodiments, at least one of the first tab portion and the second tab portion comprise at least one living hinge to provide flexibility to the base member.

In certain embodiments, the base member is attachable to the person using medical-grade adhesive affixed to a side of the base member that is placed against the person at the tube insertion site, the medical-grade adhesive comprising a peel-off cover for exposing an adhesive portion of the medical-grade adhesive that adheres to the person.

In some embodiments, the base member is shaped to correspond to a shape of the person's body where the tube insertion site is located. A system for a medical tube securement device, in one embodiment, includes a tube securement apparatus and a means for attaching the base member to the location of the tube insertion site on the person.

The tube securement apparatus, in certain embodiments, comprises a base member and a clamping member. In one embodiment, the base member includes a first tab portion, a second tab portion, and an opening for receiving a tube. In certain embodiments, the opening is located substantially between the first tab portion and the second tab portion.

A clamp member, in one embodiment, secures the tube within the opening to prevent the tube from moving while the base member is attached to a person and the tube is located at a tube insertion site on the person. In some embodiments, the means for attaching the base member to the location of the tube insertion site on the person comprises a strap.

In certain embodiments, the system further comprises an opening on the first tab portion for fastening one end of the strap and a protrusion on the second tab portion that is configured to receive a corresponding loop on the strap.

In various embodiments, the system further comprises a bite block member, the bite block member configured to prevent the person's mouth from closing when the tube securement apparatus is used to secure a tube for intubation.

In further embodiments, the bite block member extends from a side of the base member that is placed against the person's mouth to a location within the person's mouth that prevents the person from closing their mouth while the tube is within the person's mouth.

In certain embodiments, the bite block member is formed as part of the base member such that the bae member and the bite clock member comprise a unitary body. In some embodiments, the bite block member is separate from the base member and is selectively coupleable to the base member for use in intubation. In certain embodiments, the bite block member comprises an opening for receiving the tube such that the tube passes through the bite block member.

A method for a medical tube securement device includes attaching a tube securing apparatus to a tube insertion site, inserting the tube within the opening in the base member at the tube insertion site, and securing the tube within the opening in the base member using the clamp member.

The tube securement apparatus, in certain embodiments, comprises a base member and a clamping member. In one embodiment, the base member includes a first tab portion, a second tab portion, and an opening for receiving a tube. In certain embodiments, the opening is located substantially between the first tab portion and the second tab portion. A clamp member, in one embodiment, secures the tube within the opening to prevent the tube from moving while the base member is attached to a person and the tube is located at a tube insertion site on the person.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B and C.

The subject matter disclosed herein is directed to a device for securing a medical tube to a person's body, such as an endotracheal tube, a tracheostomy tube, a gastrostomy tube, a feeding tube, an intravenous tube, and/or the like. Securing a tube to a person's body without a tube fastener can be a cumbersome undertaking and may be prone to failure at inopportune moments during medical operations or daily life, e.g., in the event of an emergency. As such, tube fasteners may generally be used to secure a medical tube to a tube insertion site. However, existing tube fasteners may have many drawbacks such as being large, cumbersome, complex, having multiple moving parts, requiring assembly, or using adhesives that do not stick well in the presence of bodily fluids.

Presently, there is no solution for a tube securement device that is ergonomic, effective, and inexpensive. The subject matter disclosed herein seeks to provide a solution to the foregoing problems by providing a device that can clamp to a tube in a simple step, by having an adjustable open portion that can be resized with tabs/handles. This device may be cost-effective to manufacture, reliable, user friendly, and easily stored for shipping and/or storage by the end user—such as by hospital supply facilities, emergency medical services ("EMS"), or by emergency medical technicians ("EMTs") in field packs.

Figure 1:
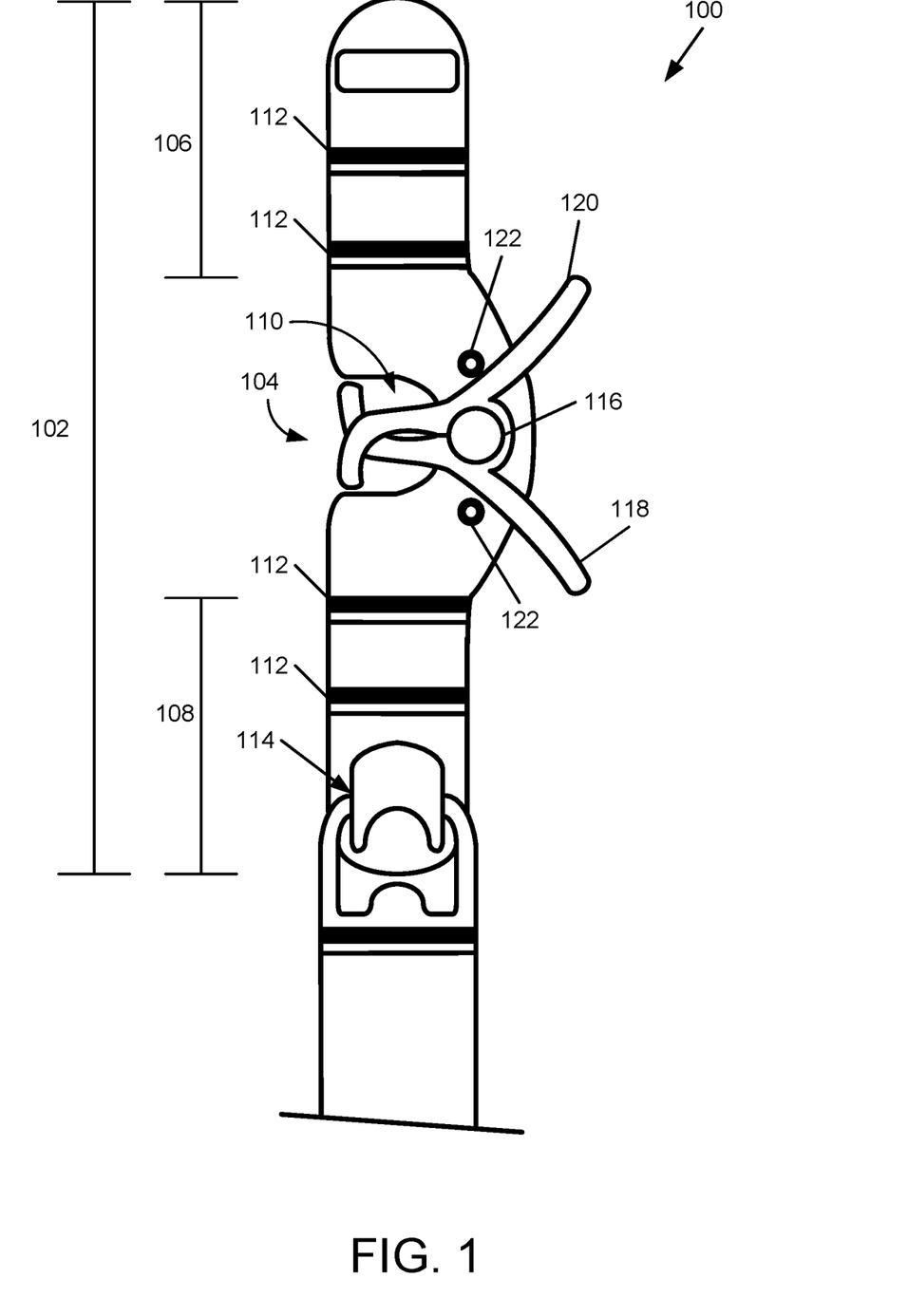
FIG. 1 is a top perspective view illustrating one embodiment of a medical tube securement device.

FIG. 1 is a top perspective view illustrating one embodiment of a medical tube securement device 100. As used herein, a medical tube securement device 100 may refer to a device of the present disclosure that is used to secure a medical tube at a person's medical tube insertion site. The medical tube may include an endotracheal tube, a tracheostomy tube, a gastrostomy tube, a feeding tube, an intravenous tube, and/or the like. The medical tube securement device 100, in one embodiment, includes a base member 102 and a clamping member 104.

In one embodiment, the base member 102 comprises a first tab portion 106, a second tab portion 108, and an opening 110, wherein the opening 110 is located substantially between the first tab portion 106 and the second tab portion 108. As used herein, a base member 102 may refer to a device of the present disclosure that is placed near a person's medical tube insertion site on a surface of the person, e.g., the person's skin, and is configured for securing a medical tube that is inserted into the insertion site.

The opening 110 may comprise a cut-out, channel, groove, or the like that is designed to allow a medical tube to pass through. In some embodiments, the opening 110 may be U-shaped, V-shaped, semi-circular, polygonal, or some combination thereof. In other embodiments, the opening 110 may comprise a fully enclosed opening, e.g., an opening that is enclosed by the base member 102 and forms a shape, e.g., a circle, that the medical tube may be inserted into.

Each of the first tab portion 106 and the second tab portion 108 may comprise one or more living hinges 112, wherein the living hinges 112 give each tab portion 106, 108 more flexibility. As used herein, living hinges 112 may refer to areas of the base member 102 where a portion of the material of the base member 102 is removed in order to increase flexibility while simultaneously maintaining enough rigidity for the base member 102 to retain a shape.

In one embodiment, the living hinge 112 may comprise a groove across the base member 102. In other embodiments, the living hinge 112 may comprise a channel, a cutout, a crevice, or the like. One of skill in the art will recognize, in light of this disclosure, that various numbers of living hinges 112 may be used for the desired flexibility. The desired flexibility may depend on the location of the tube insertion site, as a tube securement device 100 for a person's arm or neck likely requires more flexibility than a tube securement device 100 for a person's back or chest.

The second tab portion may further comprise a protrusion 114 for attaching a strap device. In some embodiments, the protrusion 114 comprises a rigid hook-like structure that may receive a loop structure and hold the loop structure in place.

In certain embodiments, the base member 102 is shaped to correspond to a shape of the person's body where the tube insertion site is located. For example, the shape of the base member 102 may change depending on the location of the tube insertion site, e.g., base members 102 for an arm, wrist, neck, back, and chest may all have different shapes configured to be applied to their respective tube insertion site, e.g., may be formed to have a predefined curvature, rigidity, flexibility, and/or the like.

In one embodiment, the clamping member 104 may comprise a fastening member 116, a first arm portion 118, and a second arm portion 120. As used herein, a clamping member 104 may refer to a device of the present disclosure that is used to keep a medical tube from moving while the medical tube securement device 100 is attached to a person at a tube insertion site on the person.

The fastening member 116, in one embodiment, couples the clamping member 104 to the base member 102 and allows the first arm portion 118 and second arm portion 120 to rotate around it. The fastening member 116 may be a rivet, a screw, an axel, or the like. The first arm portion 118 and second arm portion 120 each comprise a handle, tab, or the like at one end and prongs or claw- or fork-like structures on the opposite side, as shown in more detail in FIG. 2. In such an embodiment, a user may press the handles of the arm portions 118, 120 together to allow the user to insert the medical tube between the claw-like structures of the arm portions 118, 120. In one embodiment, the clamping member 104 and the opening 110 are substantially positioned so that a medical tube may pass through both the clamping member 104 and the opening 110 at the same time.

In one embodiment, the medical tube securement device 100 further comprises a stopper 122 on both the first tab portion 106 and the second tab portion 108 of the base member 102. The stopper 122, in certain embodiments, protrudes from the base member 102 and is structurally strong or rigid enough to resist pressure from the clamping member 104. In some embodiments, as the fastening member 116 allows the first arm portion 118 and the second arm portion 120 of the clamping member 104 to rotate, the stoppers 122 may limit the range of their rotation. In certain embodiments, the stoppers 122 may be configured so that the prongs or claw- or fork-like portions of the arm portions 118, 120 are maintained near the opening 110. As one of skill in the art will recognize, the stoppers 122 may be placed in different locations on the base member 102 to allow a desired maximum rotation angle and/or range of the arm portions 118, 120 and/or symmetry of rotation.

In certain embodiments, the medical tube securement device 100 further comprises a bite block member (not shown), wherein the bite block member is configured to prevent the person's mouth from closing when the medical tube securement device 100 is used to secure a tube for intubation. As used herein, the bite block member may refer to a solid structure that fits against a person's teeth and prevents the mouth of the person from closing. In some embodiments, the bite block member is used to keep an airway open, protect any medical tubes or other devices that may be inserted into the person's mouth from bite damage, and/or protect the person from bite or teeth-grinding damage.

In certain embodiments, the base member 102 further comprises a bite block wherein the bite block extends from a side of the base member that is placed against the person's mouth to a location within the person's mouth that prevents the person from closing their mouth while the tube is within the person's mouth.

In certain embodiments, the bite block member is formed as part of the base member 102 such that the base member 102 and the bite block member comprise a unitary body. In some embodiments, the bite block member is separate from the base member 102 and is selectively couplable to the base member for use in intubation. In further embodiments, the bite block member comprises an opening for receiving the tube such that the tube passes through the bite block member.

Figure 2:
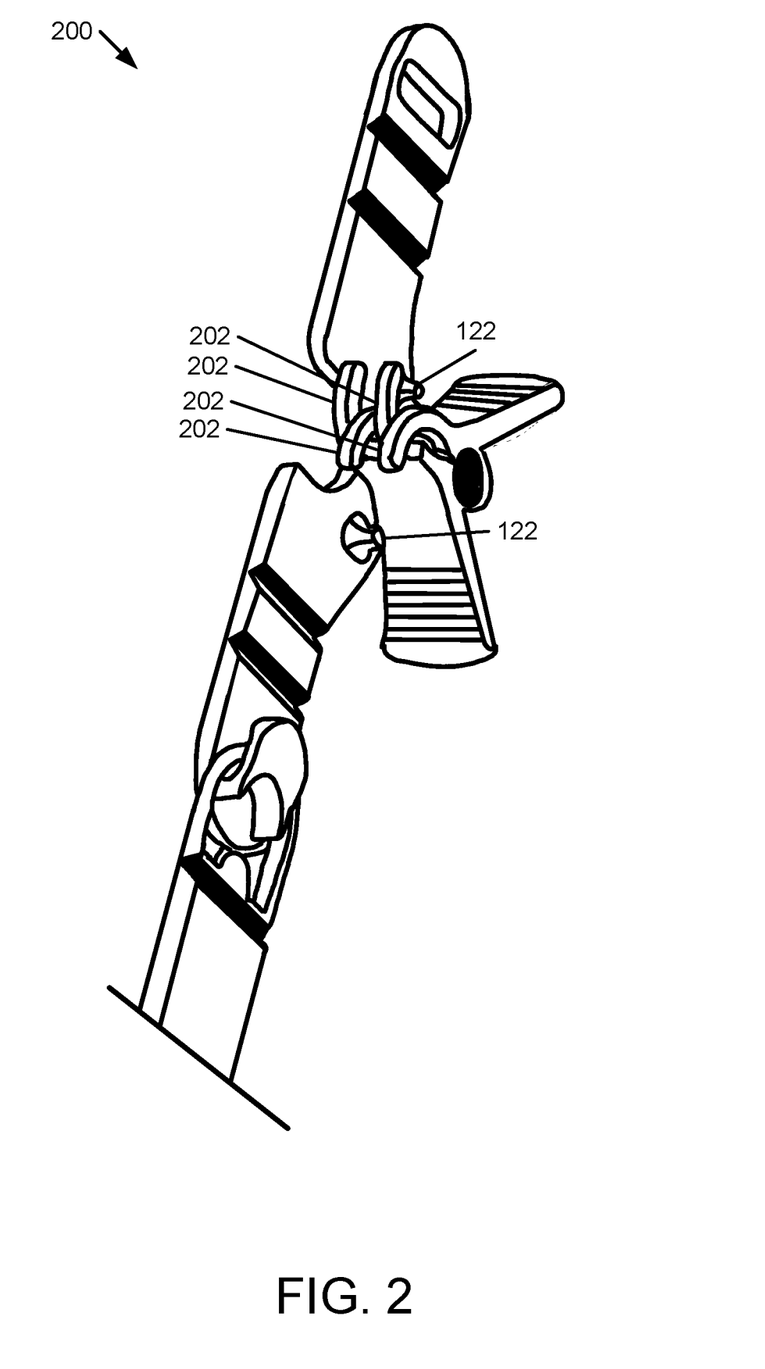
FIG. 2 is a perspective view further illustrating another embodiment of a medical tube securement device.

FIG. 2 is an angled perspective view further illustrating another embodiment of a medical tube securement device 200. In one embodiment, the medical tube securement device 200 is substantially similar to the medical tube securement device 100 described above with reference to FIG. 1.

In some embodiments, the medical tube securement device 200 further comprises one or more prongs 202 of the first arm portion 118 and second arm portion 120 of the clamping member 104. One of skill in the art will recognize, in light of this disclosure, that various numbers and sizes of prongs 202 may be used depending on the size of the tube to be secured, the desired area of pressure on the tube, and/or many other factors.

In one embodiment, the prongs 202 may include a liner such as a rubber or vinyl coating that helps secure the medical tube within the clamping member 104 and prevents the medical tube from sliding out of place. In certain embodiments, the prongs 202 may be configured to secure generic medical tubes that have internal diameters within a range of 5 millimeters to 8 millimeters. In other embodiments, the prongs 202 may be configured to secure generic medical tubes of sizes both smaller than 5 millimeters in diameter and larger than 8 millimeters in diameter.

Figure 3:
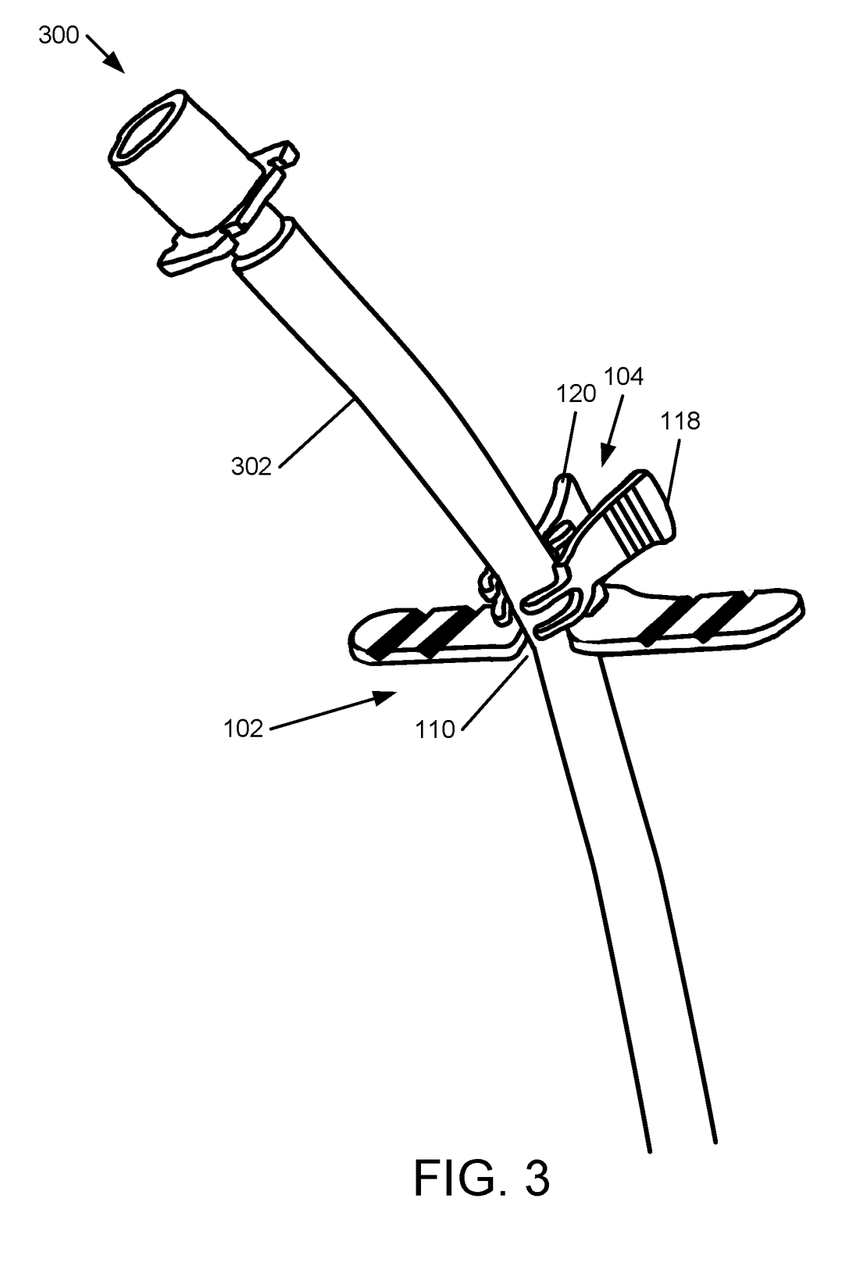
FIG. 3 is a perspective view illustrating the functionality of an embodiment of a medical tube securement device.

FIG. 3 is a perspective view illustrating an example embodiment of a medical tube securement device 300 attached to a medical tube 302. In one embodiment, the medical tube securement device 300 may be substantially similar to the medical tube securement devices described above with reference to FIGS. 1 and 2.

In such an embodiment, the medical tube securement device 300 attaches to the medical tube 302 by pressing the clamping member arms 118, 120 together to open the prongs 202, placing the medical tube within the opening 110 of the base member 102, and releasing the clamping member arms 118, 120 such that the prongs 202 apply pressure against the medical tube 302 to keep the medical tube in place within the opening 110 in the base member 102 while refraining from substantially impacting the functionality of the medical tube 302.

In other embodiments, the prongs 202 of the first arm portion 118 and second arm portion 120 interlace and/or overlap with each other to provide a more secure attachment to the medical tube 302, e.g., in certain embodiments, the prongs may enclose the medical tube 302. As one of skill in the art will recognize, the prongs 202 may have different lengths depending on the diameter of the medical tube 302 and a desired amount of overlap of the prongs 202.

Figure 4:
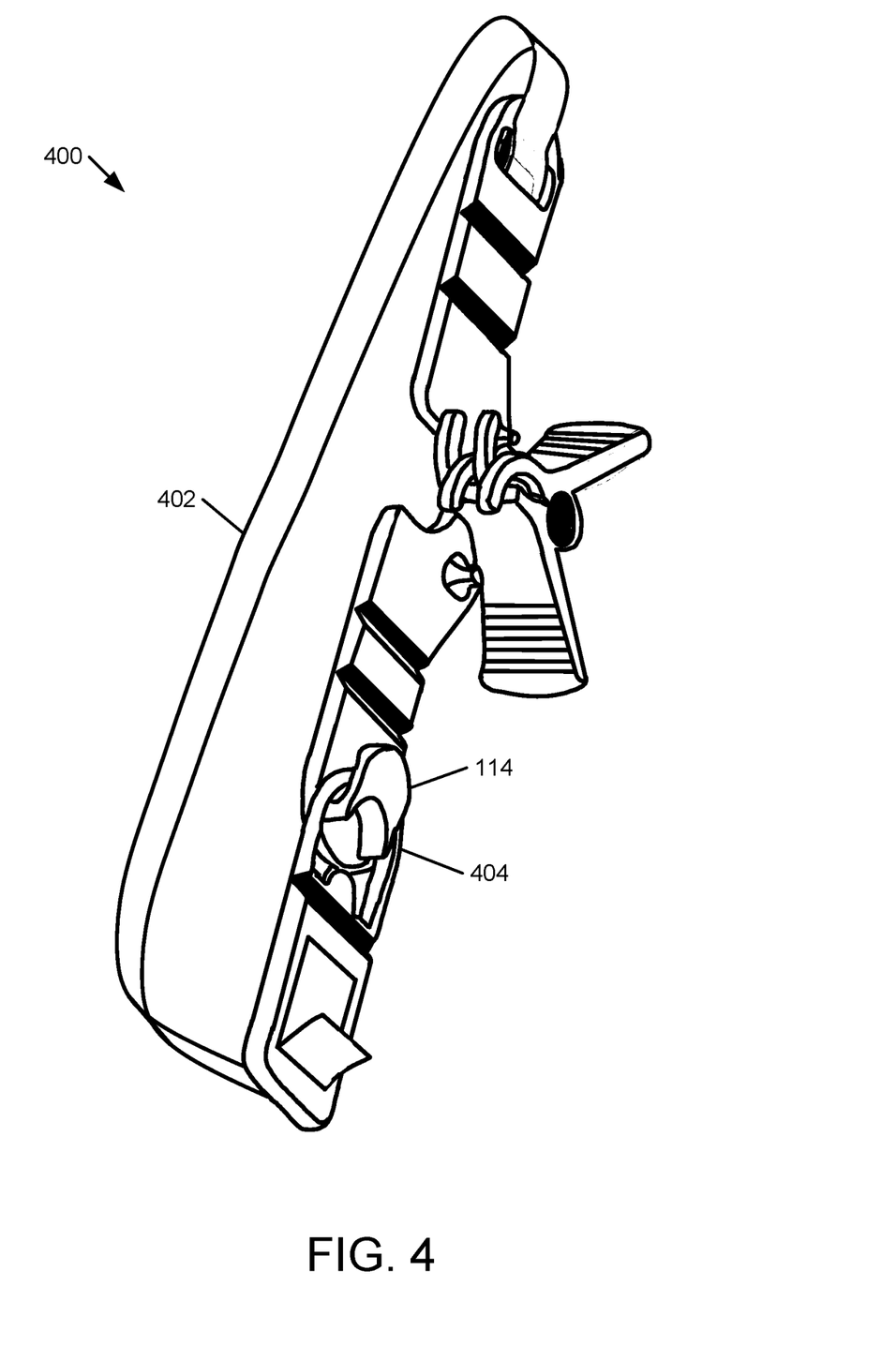
FIG. 4 is a perspective view further illustrating another embodiment of a medical tube securement device.

FIG. 4 a perspective view further illustrating another embodiment of a medical tube securement device 400. In one embodiment, the medical tube securement device 400 is substantially similar to the medical tube securement devices described above with reference to FIGS. 1-3.

In one embodiment, the medical tube securement device 400 further comprises a strap 402, which is attached to the first tab portion 106 of the base member 102. In some embodiments, the means of attachment between the strap 402 and the first tab portion 106 comprises a strap cinch, a sewn loop, and/or the like.

The strap 402, in one embodiment, comprises a loop structure 404 at one end that attaches to the protrusion 114 of the second tab portion 108 of the base member 102. The loop structure 404 comprises a rigid structure with a fully enclosed opening large enough for the protrusion 114 to pass through. In some embodiments, the means of attachment between the strap 402 and the loop structure 404 includes a strap cinch, a sewn loop, and/or the like. In some embodiments, the strap 402 is placed around a body part of a user, e.g., a neck, arm, leg, chest, or the like, while the medical tube securement device 400 is placed at the user's tube insertion site. The strap 402 may be adjusted, e.g., tightened to secure the medical tube securement device 400 at the tube insertion site and loosened to remove the medical tube securement device 400.

Figure 5:
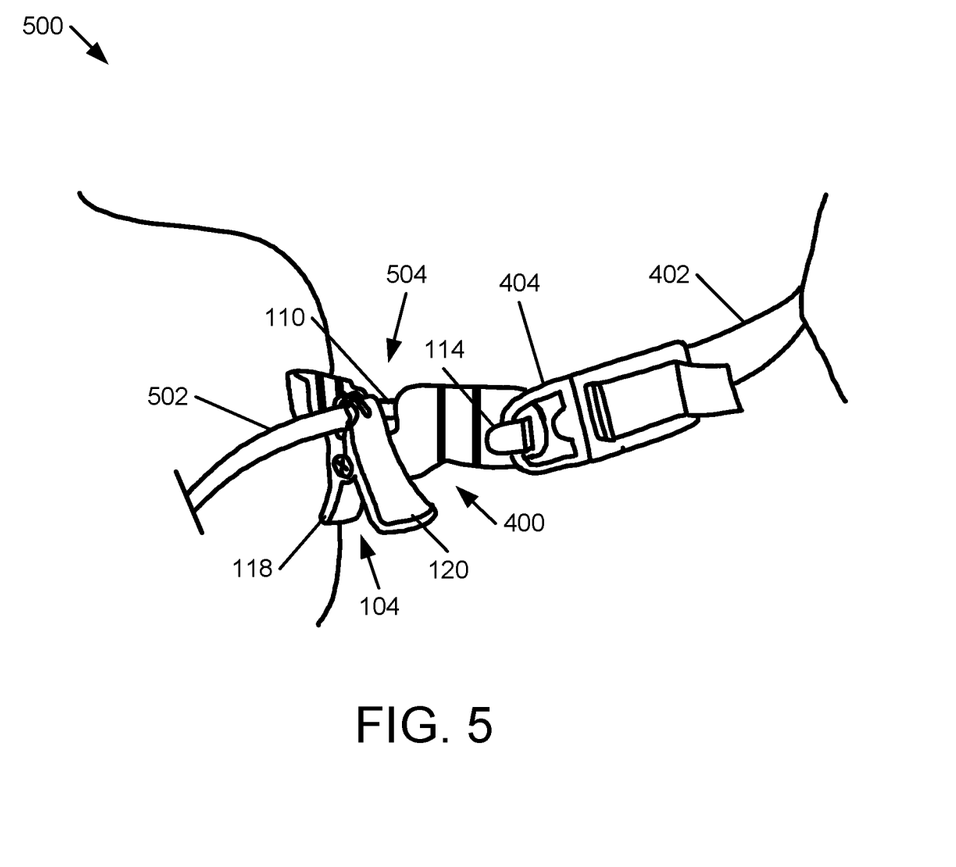
FIG. 5 a perspective view further illustrating the functionality of another embodiment of a medical tube securement device.

FIG. 5 is a perspective view further illustrating an example embodiment of securing a medical tube to a person using a medical tube securement device 400. FIG. 4 shows one embodiment of the medical tube securement device 400 attached to an endotracheal tube 502 at the endotracheal tube insertion site 504.

In the depicted embodiment, the medical tube securement device 400 attaches to the endotracheal tube 502 by pressing the clamping member arms 118, 120 together to open the prongs 202, placing the endotracheal tube 502 within the opening 110 of the base member 102, and releasing the clamping member arms 118, 120 such that the prongs 202 apply pressure against the endotracheal tube 502 to keep the endotracheal tube 502 in place within the opening in the base member 102 while refraining from substantially affecting the functionality of the endotracheal tube 502.

In other embodiments, the prongs 202 of the first arm portion 118 and second arm portion 120 overlap with each other to provide a more secure attachment to the endotracheal tube 502. As one of skill in the art will recognize, the prongs 202 may have different lengths depending on the diameter of the endotracheal tube 502 and a desired amount of overlap of the prongs 202.

In some embodiments, the medical tube securement device 400 may be secured adjacent to the endotracheal tube insertion site by a strap 402. In such an embodiment, the strap 402 is secured around a user's neck by attaching a loop 404 of the strap 402 to a protrusion 114 of the base member 102.

In other embodiments, the medical tube securement device 400 may comprise an adhesive substance, such as a medical-grade adhesive substance, with a peel-off cover. To secure the medical tube securement device 200 to a tube insertion site, the peel-off cover may be peeled off and the exposed adhesive substance of the medical tube securement device 200 pressed against the person's skin at the tube insertion site.

Figure 6:
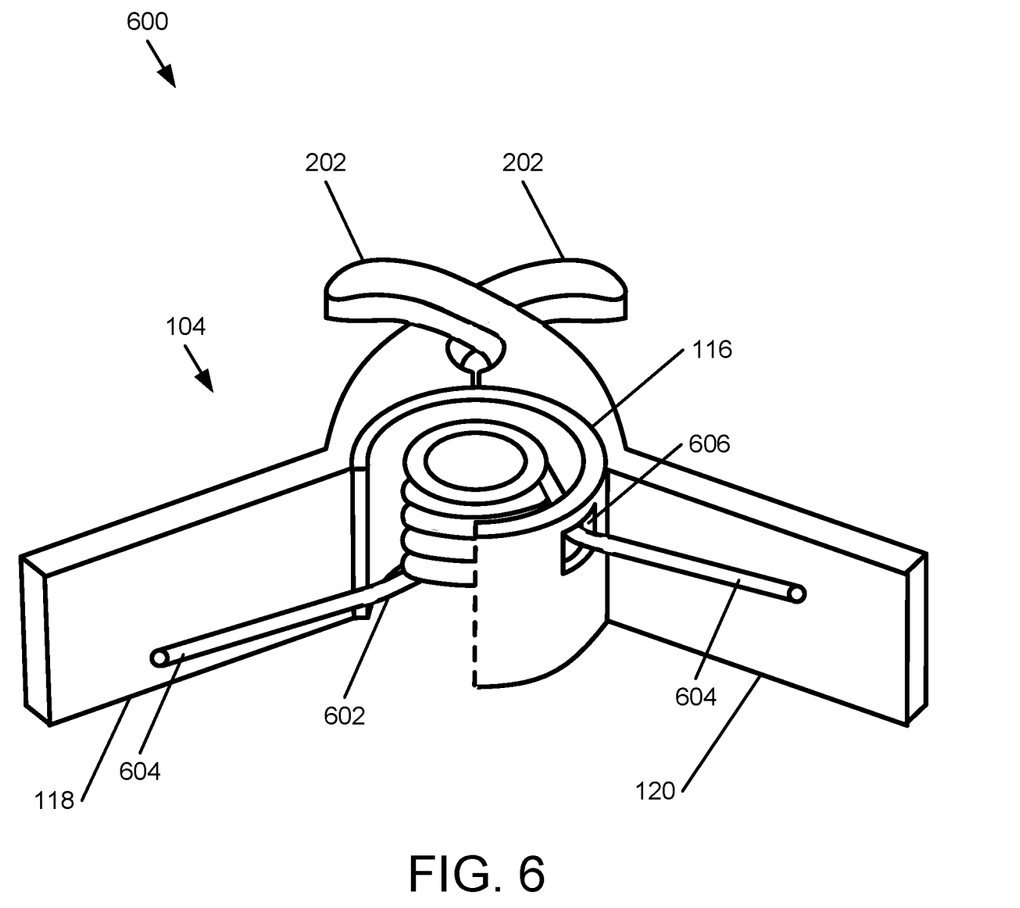
FIG. 6 is a perspective view illustrating an embodiment of a clamping member of a medical tube securement device.

FIG. 6 is a perspective view illustrating an embodiment of a clamping member 104 of a medical tube securement device, such as the tube securement device 100 described above with reference to FIG. 1. In some embodiments, the clamping member 104 comprises a first arm portion 118, a second arm portion 120, and a spring member 602.

In some embodiments, the two ends of the arm portions 118, 120 may comprise ridges or the like to provide enhanced friction between the arm portions 118, 120 and a clamped medical tube and/or the fingers of a user. In some embodiments, the spring member 602 applies pressure to the arm portions 118, 120 to push the prongs 202 together, which in turn allows the arm portions 118, 120 to apply pressure to an inserted medical tube.

In some embodiments, the ends 604 of the spring member 602 are attached to the arm portions 118, 120 by one or more of adhesive, friction, and a hole 606 in the arm portions 118, 120 and fastening member 116 where the ends 604 of the spring member 602 may be inserted. In some embodiments, the ends of the spring member 602 may be embedded within the arm portions 118, 120.

In some embodiments, the spring member 602 allows the clamping member 104 to maintain pressure against a medical tube 302 when attached. The spring member 602 does this by pushing the claw-like portions 202 on the first arm portion 118 and second arm portion 120 toward each other. The spring member 602 may be embodied as a torsion spring, a flat spring, a compression spring, a spiral spring, a tension spring, or the like.

In some embodiments, the first arm portion 118 and second arm portion 120 further comprise one or more prongs 202. One of skill in the art will recognize, in light of this disclosure, that various numbers and sizes of prongs 202 may be used depending on the size or weight of the tube and/or the relative security needed for the tube securement.

Figure 7:
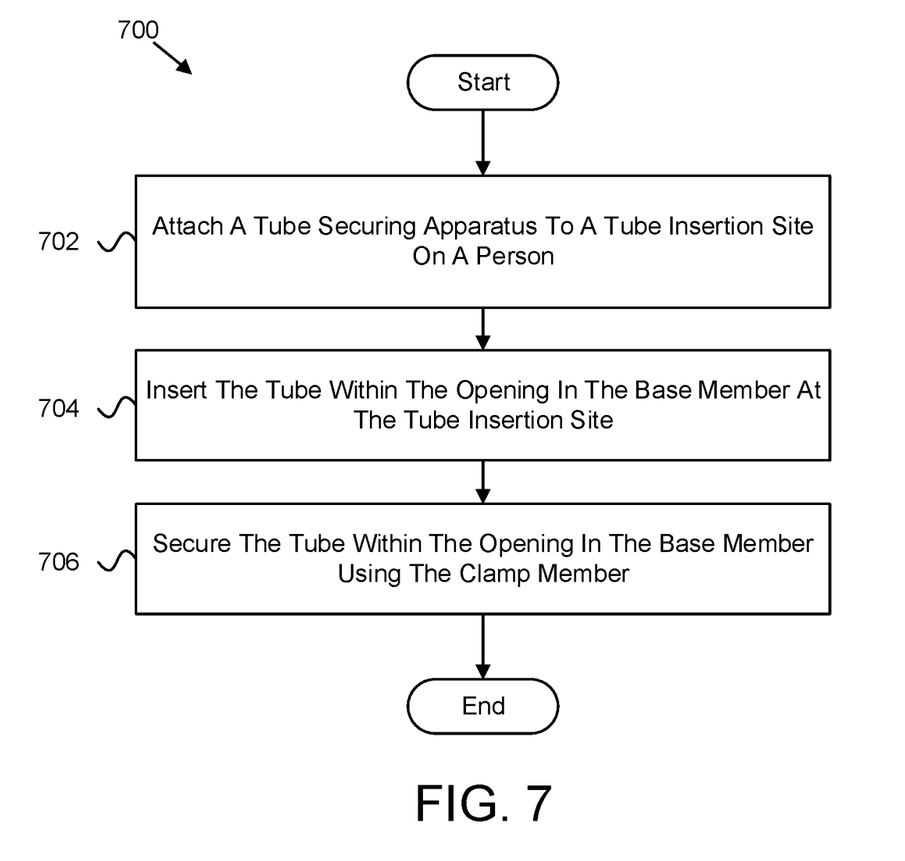
FIG. 7 is a flowchart illustrating a method of using a medical tube securement device.

FIG. 7 depicts a schematic flow-chart diagram illustrating one embodiment of a method 700 for using a tube securing apparatus. In one embodiment, the method 700 begins and attaches 702 a tube securing apparatus to a tube insertion site on a person. In certain embodiments, the method 700 inserts 704 a tube within an opening in a base member of the tube securing apparatus at the tube insertion site. In certain embodiments, the method 700 secures 706 the tube within the opening in the base member of the tube securing apparatus using the clamp member, and the method 700 ends.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
    a base member comprising:
        a front surface, a rear surface, a top surface and a bottom surface, the rear surface and the top surface are positioned between the top surface and the bottom surface;
        a first tab portion comprising a first stopper that protrudes from the first tab and the front surface;
        a second tab portion comprising a second stopper that protrudes from the second tab and the front surface, wherein the first stopper and the second stopper are positioned between the top surface of the base member and the bottom surface of the base member and spaced from the entire bottom surface of the base member; and
        an opening for receiving a tube, wherein the opening comprises a U-shaped groove that is formed by a recess of the top surface, the opening extending through the rear surface and the front surface, the opening located substantially between the first tab portion and the second tab portion; and
    a clamp member attached to the front surface and configured to secure the tube within the opening of the base member to prevent the tube from moving while the base member is attached to a person and the tube is configured to be located at a tube insertion site on the person, the clamp member comprising a first arm and a second arm that are each rotatable, the first arm comprising a first prong and a first arm end portion positioned opposite of the first prong, the second arm comprising a second prong and a second arm end portion positioned opposite of the second prong, the clamp member includes a torsion spring that is coupled to both the first and second arms and is configured to cause the first and second arms to maintain pressure against the tube when the tube is clamped between the first and second arms, wherein the first prong and the second prong are configured to open when the first arm end portion and the second arm end portion are pressed against each other, wherein a portion of the clamp member comprising the torsion spring is positioned between the first stopper and the second stopper, the first stopper positioned to a left side of an exterior surface of the first arm and the second stopper positioned to a right side of an exterior surface of the second arm, the first prong and the second prong forming a clamp member opening that is aligned with the opening of the base member, the clamp member opening configured to receive the tube, a rotational range of the first and second arms limited by the first and second stoppers such that, when the first prong is in contact with the first stopper and the second prong is in contact with the second stopper, further rotation of the first and second prongs is prevented from going past the first and second stoppers, and a maximum rotation angle of the first and second prongs and a maximum opening size of the clamp member opening are obtained.

2. The apparatus of claim 1, wherein the first prong and the second prong are configured to interlace around the tube to secure the tube within the opening in the base member when the first and second arms apply clamping force to the tube.

3. The apparatus of claim 2, wherein the first arm and the second arm are configured to secure tubes having various sizes within the opening in the base member.

4. The apparatus of claim 3, wherein the first arm and the second arm are configured to secure medical tubes that have internal diameters within a range of 5 millimeters to 8 millimeters.

5. The apparatus of claim 2, wherein the clamp member is fastened to the base member using a fastening member such that first and second arms are rotatable about the fastening member.

6. The apparatus of claim 2, wherein the first arm comprises a third prong and the second arm comprises a fourth prong.

7. The apparatus of claim 1, wherein the base member is made of a hypoallergenic plastic material.

8. The apparatus of claim 1, wherein at least one of the first tab portion and the second tab portion comprise at least one living hinge to provide flexibility to the base member.

9. The apparatus of claim 8, wherein the first tab portion and the second tab portion each comprise two living hinges.

10. The apparatus of claim 1, wherein the base member is attachable to the person using medical-grade adhesive affixed to a side of the base member that is placed against the person at the tube insertion site, the medical-grade adhesive comprising a peel-off cover for exposing an adhesive portion of the medical-grade adhesive that adheres to the person.

11. The apparatus of claim 1, wherein the base member is shaped to correspond to a shape of the person's body where the tube insertion site is located.

12. A system, comprising:
    an apparatus, comprising:
        a base member comprising:
            a front surface, a rear surface, a top surface and a bottom surface, the rear surface and the top surface are positioned between the top surface and the bottom surface;
            a first tab portion comprising a first stopper that protrudes from the first tab and the front surface;
            a second tab portion comprising a second stopper that protrudes from the second tab and the front surface, wherein the first stopper and the second stopper are positioned between the top surface of the base member and the bottom surface of the base member and spaced from the entire bottom surface of the base member; and
            an opening for receiving a tube, wherein the opening comprises a U-shaped groove that is formed by a recess of the top surface, the opening extending through the rear surface and the front surface, the opening located substantially between the first tab portion and the second tab portion; and
        a clamp member attached to the front surface and configured to secure the tube within the opening of the base member to prevent the tube from moving while the base member is attached to a person and the tube is configured to be located at a tube insertion site on the person, the clamp member comprising a first arm and a second arm that are each rotatable, the first arm comprising a first prong and a first arm end portion positioned opposite of the first prong, the second arm comprising a second prong and a second arm end portion positioned opposite of the second prong, the clamp member includes a torsion spring that is coupled to both the first and second arms and is configured to cause the first and second arms to maintain pressure against the tube when the tube is clamped between the first and second arms, wherein the first prong and the second prong are configured to open when the first arm end portion and the second arm end portion are pressed against each other, wherein a portion of the clamp member comprising the torsion spring is positioned between the first stopper and the second stopper, the first stopper positioned to a left side of an exterior surface of the first arm and the second stopper positioned to a right side of an exterior surface of the second arm, the first prong and the second prong forming a clamp member opening that is aligned with the opening of the base member, the clamp member opening configured to receive the tube, a rotational range of the first and second arms limited by the first and second stoppers such that, when the first prong is in contact with the first stopper and the second prong is in contact with the second stopper, further rotation of the first and second prongs is prevented from going past the first and second stoppers, and a maximum rotation angle of the first and second prongs and a maximum opening size of the clamp member opening are obtained; and a means for attaching the base member to the location of the tube insertion site on the person.

13. The system of claim 12, wherein the means for attaching the base member to the location of the tube insertion site on the person comprises a strap.

14. The system of claim 13, wherein the base member comprises an opening on the first tab portion for fastening one end of the strap and a protrusion on the second tab portion that is configured to receive a corresponding loop on the strap.

15. The system of claim 13, wherein the strap comprises at least one living hinge.

16. A method, comprising:
attaching a tube securing apparatus to a tube insertion site on a person, the tube securing apparatus comprising:
 a base member comprising:
  a front surface, a rear surface, a top surface and a bottom surface, the rear surface and the top surface are positioned between the top surface and the bottom surface;
  a first tab portion comprising a first stopper that protrudes from the first tab and the front surface;
  a second tab portion comprising a second stopper that protrudes from the second tab and the front surface, wherein the first stopper and the second stopper are positioned between the top surface of the base member and the bottom surface of the base member and spaced from the entire bottom surface of the base member; and
  an opening for receiving a tube, wherein the opening comprises a U-shaped groove that is formed by a recess of the top surface, the opening extending through the rear surface and the front surface, the opening located substantially between the first tab portion and the second tab portion; and
 a clamp member attached to the front surface and configured to secure the tube within the opening of the base member to prevent the tube from moving while the base member is attached to a person and the tube is configured to be located at a tube insertion site on the person, the clamp member comprising a first arm and a second arm that are each rotatable, the first arm comprising a first prong and a first arm end portion positioned opposite of the first prong, the second arm comprising a second prong and a second arm end portion positioned opposite of the second prong, the clamp member includes a torsion spring that is coupled to both the first and second arms and is configured to cause the first and second arms to maintain pressure against the tube when the tube is clamped between the first and second arms, wherein the first prong and the second prong are configured to open when the first arm end portion and the second arm end portion are pressed against each other, wherein a portion of the clamp member comprising the torsion spring is positioned between the first stopper and the second stopper, the first stopper positioned to a left side of an exterior surface of the first arm and the second stopper positioned to a right side of an exterior surface of the second arm, the first prong and the second prong forming a clamp member opening that is aligned with the opening of the base member, the clamp member opening configured to receive the tube, a rotational range of the first and second arms limited by the first and second stoppers such that, when the first prong is in contact with the first stopper and the second prong is in contact with the second stopper, further rotation of the first and second prongs is prevented from going past the first and second stoppers, and a maximum rotation angle of the first and second prongs and a maximum opening size of the clamp member opening are obtained; and inserting the tube within the opening in the base member at the tube insertion site; and securing the tube within the opening in the base member using the clamp member.

\* \* \* \* \*